(12) United States Patent
Mak et al.

(10) Patent No.: US 10,048,257 B2
(45) Date of Patent: *Aug. 14, 2018

(54) SIGNAL AMPLIFICATION MICROSPHERES, THEIR USE IN ONE-STEP AND MULTI-STEP ANALYTICAL AMPLIFICATION PROCEDURES AND METHODS FOR THEIR PRODUCTION

(71) Applicant: Supernova Diagnostics, Inc., Germantown, MD (US)

(72) Inventors: Wing Cheung Mak, Hong Kong (CN); Ling Wai Wong, Hong Kong (CN); Pui Yee Cangel Chan, Hong Kong (CN); Reinhard Renneberg, Hong Kong (CN)

(73) Assignee: Supernova Diagnostics, Inc., Germantown, MD (US)

( * ) Notice: Subject to any disclaimer, the term of this patent is extended or adjusted under 35 U.S.C. 154(b) by 232 days.

This patent is subject to a terminal disclaimer.

(21) Appl. No.: 14/837,501

(22) Filed: Aug. 27, 2015

(65) Prior Publication Data

US 2016/0047802 A1 Feb. 18, 2016

Related U.S. Application Data

(63) Continuation of application No. 13/375,108, filed as application No. PCT/GB2010/001144 on Jun. 10, 2010, now Pat. No. 9,151,748.

(30) Foreign Application Priority Data

Jun. 10, 2009 (GB) .................................. 0910010.8

(51) Int. Cl.
*G01N 33/543* (2006.01)

(52) U.S. Cl.
CPC .............................. *G01N 33/54313* (2013.01)

(58) Field of Classification Search
None
See application file for complete search history.

(56) References Cited

U.S. PATENT DOCUMENTS

| | | |
|---|---|---|
| 4,703,017 A | 10/1987 | Campbell et al. |
| 4,837,168 A | 6/1989 | de Jaeger et al. |
| 4,874,710 A | 10/1989 | Piran |
| 5,271,961 A | 12/1993 | Mathiowitz et al. |
| 5,580,749 A * | 12/1996 | Hughes ............. C12Q 1/00 435/18 |
| 5,665,383 A | 9/1997 | Grinstaff et al. |
| 5,686,113 A | 11/1997 | Speaker et al. |
| 5,756,362 A | 5/1998 | Durst et al. |
| 6,013,531 A | 1/2000 | Wang et al. |
| 6,616,946 B1 | 9/2003 | Meier et al. |
| 7,348,399 B2 | 3/2008 | Haynie |

FOREIGN PATENT DOCUMENTS

| | | |
|---|---|---|
| DE | 197 03 718 A1 | 7/1997 |
| EP | 1 309 867 B1 | 11/2006 |
| WO | WO 89/03674 | 5/1989 |
| WO | WO 95/08772 | 3/1995 |
| WO | WO 02/12888 A2 | 2/2002 |
| WO | WO 03/054546 A2 | 7/2003 |
| WO | WO 03/078659 A2 | 9/2003 |
| WO | WO 03104424 A2 * | 12/2003 ............. C12Q 1/682 |

OTHER PUBLICATIONS

King-Keung Sin et al., *Analytical and Bioanalytical Chemistry*, vol. 384, No.3 , pp. 638-644 (2006).
Mujumdar et al., *Cytometry*, 10:11-19 (1989).
Mujumdar, *Bioconjugate Chem*, 4:105-111 (1993).
PCT/GB2010/001144 International Search Report dated Feb. 11, 2010 by A. Gall of European Patent Office.
Quan et al., Intl Journal of Pharmaceutics, 359:205-10 (2008).
Southwick et al., *Cytometry*, 11:418-430 (1990).
Taton et al., *Science*, 289:1757-60 (2000).
Volodkin et al., *Biomacromolecules*, 5:1962-72 (2004).

* cited by examiner

*Primary Examiner* — Robert J Yamasaki
(74) *Attorney, Agent, or Firm* — RatnerPrestia (57) ABSTRACT

The present invention relates to microspheres comprising protein signal precursor molecules, or a carrier protein bonded to signal precursor molecules, wherein said signal precursor molecules are activatable to generate a detectable signal while remaining bonded to the carrier protein. Also disclosed is a method of making such microspheres comprising the steps of mixing protein molecules with a matrix former in solution; adding a reducing reagent to the mixture; removing the reducing reagent; and removing the matrix former to leave microspheres of protein molecules. Also disclosed are bioassay methods using the microspheres to provide signal amplification, including an amplification cycling procedure.

3 Claims, 5 Drawing Sheets

SIGNAL AMPLIFICATION MICROSPHERES, THEIR USE IN ONE-STEP AND MULTI-STEP ANALYTICAL AMPLIFICATION PROCEDURES AND METHODS FOR THEIR PRODUCTION

CROSS-REFERENCE TO RELATED APPLICATION

This application is a Continuation of U.S. application Ser. No. 13/375,108, filed Feb. 22, 2012 which is a U.S. National Phase Application of PCT International Application PCT/GB2010/001144, filed Jun. 10, 2010 which claims priority benefit of Great Britain application number GB 0910010.8, filed Jun. 10, 2009, the contents of which are incorporated herein by reference in their entireties for all purposes.

FIELD OF THE INVENTION

The present invention relates to protein microspheres comprising protein carrier molecules and signal precursor molecules and methods of production thereof, and also to the use of such protein microspheres in in vitro bioassays for the detection of target species in a sample. The invention also relates to a method of improving the level of sensitivity of in vitro bioassays using detection techniques including but not limited to optical, magnetic, electrochemical or chemical methods. A detection method, both a direct and a powerful sequential signal amplification method and various test kits are also provided.

BACKGROUND OF THE INVENTION

In the application of the protein microspheres of the present invention to the field of bioassays, the protein microspheres carry on the surface affinity molecules for specific recognition of and binding to target molecules in a sample. Bioassays such as enzyme-linked immunoassays (ELISA), radioimmunoassays (RIA), fluorescence immunoassays (FIA), immuno agglutination assays or DNA, RNA or genomic assays are well known and play an important role in the detection of analytes in research, the human and veterinary diagnostic field, forensic diagnosis, environmental analysis, food analysis and biodefence screening for dangerous substances in the air or in water.

Bioassays are based on the interaction of at least one labelled biomolecule with an analyte (target) to be detected. The label is the means for "visualizing" the interaction. Different kinds of labels are known and give their names to the various techniques mentioned above: enzymes in ELISAs, radio isotopes in RIAs, fluorophores in FIAs, or specific labels for Western, Southern or Northern blots. Other label types include liposomes, latex particles in immuno agglutination assays as well as dyes, mediators, gold particles.

The most important requirements for bioassays are analytical specificity and analytical sensitivity. Analytical specificity is determined by the affinity molecules, or biorecognition molecules, for example in the case of matching of the binding site of an antibody to its antigen (analyte) or the hybridisation of two complementary nucleic acid strands. Analytical sensitivity of a bioassay is also influenced by the biorecognition molecules due to the affinity constant of its biointeraction with the target species. The label acts as a marker indicating that a reaction has taken place between the target and the affinity molecule and can be measured with different techniques:

(i) optically by the measurement of the absorption of a dye or the fluorescent light emitted by fluorophores, or the luminescent light emitted by luminescent or chemiluminescent compounds, or measurement of turbidity caused by the light scattering of agglutinated latex particles;

(ii) radioactively by the measurement of radio isotopes;

(iii) electrochemically by the measurement of mediators or electroactive substances; or (iv) magnetically by the measurement of magnetic force.

(v) piezoelectrically by the measurement of changes in mass.

Radioimmunoassays, using radio isotopes as labels, are still regarded by many as the most sensitive method. This very powerful technique was introduced in 1959 by Yalow and Berson and represented a new era in analytical chemistry, diagnostics and medicine. Nevertheless, this technique has the disadvantage that the risk of harmful contamination of people and the environment cannot be eliminated altogether because of the radioactive isotopes used.

In the meantime, non-radioactive methods have been developed and improved with the aim of reaching comparable analytical sensitivity. The importance of optical methods based on fluorescence, luminescence and absorption spectroscopy has strengthened over time and is still growing.

ELISA technology uses enzymes as markers to amplify the signal. After the bioassay is performed, the biointeraction of the analyte and the probe is amplified by the production of a high number of dye molecules by one enzyme marker molecule. Enzymes such as like glucose oxidase (GOD, EC 1.1.3.4.), alkaline phosphatase (AP, EC 3.1.3.1) or peroxidase (POD, EC 1.11.1.7) may be used, with turnover numbers of 2000 substrate molecules per second ($s^{-1}$), 5000 $s^{-1}$ and 10000 $s^{-1}$, respectively. Drawbacks of the ELISA technique are the high number of steps involved in the procedure and the length of time needed for substrate incubation.

Fluorescence methods have also been employed in bioassays for many years and continue to be of high interest. All fluorescence based techniques ensure a good sensitivity and a low detection limit of $10^{-8}$ to $10^{-18}$ M. Special techniques, e.g., "time resolved fluorescence", chemi- and bioluminescence or techniques based on the energy transfer between a donor and an acceptor molecule can reach detection limits of $10^{-15}$ to $10^{-18}$ M.

The fluorescence-immunoassays known in the prior art use low molecular weight fluorescent labels with reactive functional linker groups (SOUTHWICK, P. L., et al., Cytometry, 11, pp. 418-430, 1990, MUJUMDAR, R. B., et al., Bioconjugate Chemistry, 4, pp. 105-111, 1993, MUJUMDAR, R. B., et al., Cytometry, 10, pp. 11-19, 1989), fluorescent and dye coloured particles (U.S. Pat. Nos. 4,837, 168 and 6,013,531 and international patent application no. WO 95/08772) or fluorophore spiked dendrimers (DE 197 03 718).

It is also known to employ marker-loaded liposomes for signal amplification in immunoassays (U.S. Pat. Nos. 5,756, 362, 4,874,710 and 4,703,017). In practice, the sensitivity of these methods is limited by the amount of marker substance which can be incorporated into the liposomes in solubilized form. A further drawback of using labelled liposomes is the limited stability of liposomes.

As mentioned above, it is important in bioassay development to achieve a very high analytical sensitivity, defined as the degree of signal response for a certain change in analyte concentration (slope of the calibration curve). In immunochemical determinations, whether sandwich or competitive assay types, the analytical sensitivity is dependent on the concentration range.

Another two factors affecting the analytical sensitivity are the quantity of sample necessary for the determination and the overall reaction time for the result. The higher the sample volume, and the longer the applied overall reaction time, the lower the concentration of analyte which can be detected and measured. However, in many practical situations, there is not a sufficient volume of sample available (e.g., in pharmaceutical research) or the component is distributed in a very large volume of sample (e.g., antibiotic residues in milk or a biodefensive substance in the air). Therefore, a key challenge is to detect and/or determine very small quantities of substances in the available small sample volumes, or to detect and/or determine a substance distributed at very low concentration in a large sample volume.

Consequently, the applied technology must have high analytical sensitivity, especially in the very low concentration ranges.

In order that the analytical sensitivities of the various known technologies can be compared objectively at very low concentration ranges, CLSI (Clinical and Laboratory Standards Institute and/or NCCLS in the US) has defined analytical sensitivity using 3 terms: Limit of Blank (LoB), Limit of Detection (LoD) and Limit of Quantitation (LoQ). The data for these parameters are estimated and used for comparisons between the various technologies.

To achieve high analytical sensitivities, different biolabel systems have been developed to effect signal amplification, such as enzymes biolabels, organic microcrystal biolabels and colloidal gold labels, etc.

In enzyme biolabel systems, enzyme molecules convert substrates into products with optical or electro-chemical properties. Due to a high turnover rate, such as with horseradish peroxidase, or due to a very large linear enzymatic reaction, such as with alkaline phosphatase, huge amounts of product (signal) can be generated to achieve amplification.

Another approach is the so-called "enzyme cycling" technique to amplify the detection signal which improves the assay sensitivity.

A new class of label utilizing solid particles of signal-generating substances has been disclosed in European published patent application no. EP 1309867. Billions of signal generating molecules present in each solid particle can be released instantly upon exposure to a releasing reagent to create a "Supernova Effect".

The signal amplification principle of enzyme systems is based on the conversion of enzyme substrates to generate signals that are being released into the bulk phase. The signal amplification principle of solid particle systems is based on generation and release of a large number of signal molecules into the bulk phase of a reaction chamber. However, the release of the signal molecules to the bulk phase results in a partial dilution of the signal molecule concentration and affects the analytical sensitivity.

Also known is a signal amplified bioassay using colloidal gold labelling. Taton et al. (T. Andrew Taton, Chad A. Mirkin, Robert L. Letsinger, "Scanometric DNA Array Detection with Nanoparticle Probes", Science, 289(8) 1757-1760, 2000) report a signal amplification method based on colloidal gold followed by silver enhancement, in which the colloidal gold promotes the reduction of silver(I) onto the gold particle surfaces, resulting in the accumulation of a large amount of silver metal onto the colloidal gold label. The silver enhancement approach can detect concentrations of oligonucleotides as low as 5 nanomoles per liter.

Another approach of using colloidal gold labels for amplified bioassays is based on bioaffinity-induced aggregation of colloidal gold, which results in a colour change from red to blue that can be observed with the naked eye. The bioaffinity-induced aggregation approach can detect oligonucleotides at concentration levels of 10 femtomoles per liter. The signal amplification principle of colloidal gold labelling is based on the accumulation or aggregation of signal molecules into a concentrated small volume. By comparing the signal amplification ability of the above mentioned label systems, the colloidal gold amplification system with signal molecule accumulation—fixed by another affinity molecule—at a focused area on a solid carrier (e.g., in lateral flow devices) can achieve high analytical sensitivity.

SUMMARY OF THE INVENTION

An embodiment of the present invention provides a method for detecting target molecules in a sample which ensures an excellent analytical sensitivity, a low detection limit and, optionally, a further enhancement of the detection signal by repetitive cycle amplification, sequentially applying the procedure. This approach is quite different from known methods.

Another embodiment of the invention provides various test kits for optical, electrochemical or chemical detection of target molecules in the research and diagnostic fields.

A still further embodiment of the invention provides labelled biomolecules which can be reliably prepared and which are broadly applicable in bioassays, preferably in human and veterinary diagnostic field, forensic diagnosis, environment analysis, food analysis, biodefense screening, DNA, RNA or genomic research and diagnosis.

Definitions

Affinity/Biorecognition Molecules

Affinity molecules are substances which recognise and bind by their structure or by their pore sizes or by their electrical charge specifically to another substance, with a certain affinity power (affinity/avidity constant).

There are very many different affinity molecules which may be generally used with a certain class of substances (e.g., Protein A/G for IgG-antibodies) or may be very specific for only one substance (e.g., an antibody for an antigen, a DNA-sequence for another sequence, or Avidin for Biotin, certain enzymes for their substrates).

Carrier Proteins

The carrier proteins are mainly involved in the formation of sponge-like microcapsules by opening intra-cellular S—S bonds and then allowing self-assembly formation of both inter- and intra-molecular S—S bonds; the inter-molecular S—S bonds are responsible for the structural integrity of the protein microspheres.

Examples of carrier proteins which may be used include:
Fibrous proteins (e.g., cytoskeletal, extracellular matrix proteins, etc.)
Globular proteins
Blood proteins which may be isolated from serum and plasma (e.g., hemoproteins, transport proteins, DNA binding proteins, etc.)
Lipoproteins
Glycoproteins
Immune system proteins (e.g., mono- and polyclonal antibodies, antigens, etc.)
Recombinant proteins
Genetically modified proteins Chemically modified proteins
Synthetic proteins
Mixtures of various proteins
Nutrient proteins (e.g., storage proteins, transport proteins, etc.)
Enzymes
Ribozymes In general, any sulphur-containing proteins of human, animal and plant origin, or sulphur-containing peptides (including synthetic peptides) can be used.

Signal Amplification

Any reaction between two or more substances/reaction partners leading to a physico-chemically measurable signal.

In most cases, the signal in immunochemical and hybridisation reactions is so weak that an amplification of this signal must be performed before the measurements lead to interpretable results.

The amplification can be done by various methodologies and technologies.

The present invention provides both a one-step and a multi-step amplification procedure using signal amplification microspheres. In a variant of the multi-step amplification procedure, at least one cycle of the amplification may use capsules encapsulating solid particles of signal generating organic substances and carrying on their surface affinity molecules for specific recognition of and binding to target molecules, of the type disclosed in EP 1309867, the disclosure of which is incorporated here by reference.

Microspheres

The microspheres of the present invention do not have a solid boundary and could be likened to a sponge ball with pores extending into its interior. They are a network of protein molecules which are linked together covalently.

They are formed by adsorptive binding or co-precipitation at a freshly precipitated template and by opening of the intra-molecular S—S bonds. The resulting free thiol groups are then allowed to form new inter- and intra-molecular S—S bonds, the inter-molecular S—S bonds contributing to the microsphere formation. The microspheres have a homogeneous structure and are not layered like capsules formed by a layer-by-layer technique such as those disclosed in EP 1309867.

The microspheres have a diameter between 10 nm and 1 mm, preferably 400 nm to 10 µm. Although these limits fall at least partly outside the micrometer range, the term "microspheres" will be used herein for convenience in referring to the discrete particles formed of networks of protein molecules in accordance with the present invention.

Signal Amplification Microspheres

Signal amplification microspheres are microspheres which consist of a carrier protein+a signal precursor molecule+an affinity molecule.

They have on their surface specific binding characteristics to a substance (target or analyte) to be determined.

Matrix Former

Matrix formers are materials such as calcium carbonate, calcium alginate, porous silica, oligo- or polysaccharide such as dextran that are mixed with carrier protein and/or signal precursor molecules to form microsphere templates by co-precipitation.

Reducing Reagent

The reducing reagent is a material which causes opening of the intra-molecular disulphide bonds within the protein molecules in the microsphere template. An example of a reducing reagent is dithiothreitol (DTT).

Matrix Removal Reagent

Matrix removal reagents are materials such as the chelating agent (EDTA), acids or bases that are used to remove the matrix former from the microsphere template, leaving a protein microsphere.

Signal Precursor Molecules

Signal precursor molecules are molecules which, when reacted with one or more other reagents, lead to a measurable signal. The signal precursor molecules may be of a direct or indirect type. In the case of a direct signal precursor, the signal precursor molecules themselves are changed upon activation to generate the signal to be detected. In the case of an indirect signal precursor, the signal precursor molecules react with another species upon activation and this other species may be responsible for generating the signal to be detected. The signal precursor molecules may be low molecular weight signal precursor molecules or high molecular weight signal precursor molecules.

Low Molecular Weight Signal Precursor Molecules

The signal precursor molecules may be low molecular weight substances selected from the group consisting of fluorophores and their derivatives, luminophores and their derivatives, chromophores and their derivatives, prosthetic groups, or redox active substances selected from redox mediators, electrode-active substances.

High Molecular Weight Signal Precursor Molecules

High molecular weight protein signal precursor molecules include, but are not limited to, high molecular weight substances selected from the group consisting of enzymes and their precursors, bioluminogenic and fluorogenic proteins and ribozymes; peptides or proteins selected from the group consisting of antibodies including monoclonal and polyclonal antibodies, receptors, antigens, recombinant proteins, lectins, avidins, lipoproteins and glycoproteins, nucleic acids, ribozymes and aptamers.

There are very many different substances from different chemical classes which lead via an initiated reaction to a measurable signal. The measurable signal can be based on:
 fluorimetry
 luminometry
 colour change in the ultraviolet, visible and near infrared range
 change in the redox-potential
 change in mass during complex formation or precipitation Target Molecule This term is synonymous with "analyte", which means a substance or chemical constituent that is determined in an analytical procedure, such as an immunoassay.

BRIEF DESCRIPTION OF THE DRAWINGS

The invention will now be described by way of example only with reference to the drawings, in which.

DETAILED DESCRIPTION OF THE INVENTION

In a first aspect, the invention provides microspheres comprising a carrier protein bound with signal precursor molecules, wherein the signal precursor molecules are activatable to generate a detectable signal whilst remaining bound with the carrier protein.

In an embodiment, the microspheres are hybrid or heteroparticles, by which is meant that the carrier protein and the signal precursor molecules are different. In an alternative embodiment, the microspheres are homo-particles, by which is meant that the carrier protein and the signal precursor are the same.

As indicated above, the signal precursor molecules may be of a direct or indirect type. In the case of a direct signal precursor, the signal precursor molecules themselves are changed upon activation to generate the signal to be detected. In the case of an indirect signal precursor, the signal precursor molecules react with another species upon activation and this other species may generate the signal to be detected.

Preferably, the carrier protein is selected from fibrous proteins, including but not limited to cytoskeletal proteins or extracellular matrix proteins; or globular proteins including but not limited to blood proteins, hemoproteins, cell adhesion proteins; or transport proteins, growth factors, receptor proteins, DNA-binding proteins, immune system proteins, including but not limited to mono- or polyclonal antibodies, nutrient storage/transport proteins, chaperone proteins or enzymes; or genetically modified proteins; or recombinant proteins or chemically modified protein and synthetic proteins. More preferably, the carrier protein is a protein which circulates in blood, such as bovine serum albumin. This protein is widely used in biochemical applications, including ELISAs and immunoblots. It has good stability and is available at low-cost because large quantities of it can be readily purified from bovine blood, a by-product of the cattle industry.

The signal precursor molecules may be low molecular weight substances selected from the group consisting of fluorophores and their derivatives, luminophores and their derivatives, chromophores and their derivatives, prosthetic groups, or redox active substances selected from redox mediators, electrode-active substances.

Preferably, low molecular weight signal precursor molecules are fluorophores such as fluoresceins, cyanines, carbocyanines, rhodamines, xanthenes, diazo-dye based fluorescent substances, and small fluorescent aromatic and heteroaromatic molecules.

Alternatively, the low molecular weight signal precursor molecules may be chromophores such as pyrazolone, anthraquinone, carotenoid and diazo- and monoazo, oxazine, indigoid, or riboflavine based dye substances.

Most preferably, the low molecular weight signal precursor molecules are fluorescein derivatives such as fluorescein diacetate (FDA), fluorescein diacetate isothiocyanate (FDA-isothiocyanate) or fluorescein maleimide (FDA-maleimide)

High molecular weight protein signal precursor molecules include, but are not limited to, high molecular weight substances selected from the group consisting of enzymes and their precursors, bioluminogenic and fluorogenic proteins and ribozymes; peptides or proteins selected from the group consisting of antibodies including monoclonal and polyclonal antibodies, receptors, antigens, recombinant proteins, lectins, avidins, lipoproteins and glycoproteins, nucleic acids, ribozymes and aptamers.

Preferably, high molecular weight signal precursor molecules are affinity molecules such as peptides and proteins, nucleic acid strands, carbohydrates, ligands with low molecular weight and molecular imprinted polymers (MIPs) or mixtures thereof.

Alternatively, the high molecular weight signal precursor molecules may be enzymes such as peroxidase, oxidoreductase, ligase, polymerase and transferase.

Most preferably, the high molecular weight signal precursor molecules are avidin and NeutrAvidin (Trade Mark).

The microspheres described above have dimensions in the range from 10 nm to 1 mm, preferably in the range from 400 nm to 10 µm. The structure of the microspheres is preferably substantially homogeneous; that is to say, the material forming the microspheres is substantially uniformly dispersed and they have a substantially uniform density and porosity through the body of the particles.

The microspheres resemble miniature sponge or cotton wool balls and, although they have a discernible boundary, they are not capsules having a solid outer shell that defines the boundary.

When the microspheres are combined with affinity molecules for binding to a target in solution, those affinity molecules will become attached to the microspheres, The microspheres are comprised of affinity molecules or the affinity molecules may be conjugated or bound directly or via linker molecules to the surface of the microspheres or bound/attached by adsorption. The linker molecules include, but are not limited to, biomolecules, for example avidin, streptavidin, NeutrAvidin (Trade Mark), protein A, protein G, lectin or low molecular weight cross linkers. However, some affinity molecules will diffuse into the interior of the microspheres and will become attached there too in special cases. Of course, the extent of such diffusion will depend on the relative size of the affinity molecules and the pore sizes of the microspheres.

The affinity molecules attached to the microspheres may be biorecognition molecules such as specific peptides and proteins, nucleic acid strands, carbohydrates, ligands with low molecular weight and molecular imprinted polymers (MIPs) or mixtures thereof.

The peptides or proteins may be antibodies including monoclonal and polyclonal antibodies, receptors, antigens, lectins, avidins, oligopeptides, lipoproteins, glycoproteins, peptide hormones and allergens or parts thereof. The nucleic acids may be DNA, RNAs, oligonucleotides, ribozymes, aptamers and parts thereof. Examples of carbohydrates include mono-, oligo- and poly-saccharides, glycolipids, proteo-polysaccharides and parts thereof. The low molecular weight ligands may be biotin or biotin derivatives, steroids or hormones, cofactors or coenzymes, activators, inhibitors, pseudosubstrates or prosthetic groups of enzymes, drugs, allergens or haptens.

In a second aspect, the invention provides a method of producing microspheres as defined herein, the microspheres comprising a carrier protein bound with signal precursor molecules, wherein the signal precursor molecules are activatable to generate a detectable signal whilst remaining bound with the carrier protein. The method comprises: mixing the carrier protein and the signal precursor molecules with a matrix former in solution, preferably aqueous solution, by stirring; adding a small molecule reducing reagent with stirring; washing to remove the small molecule reducing reagent; adding a matrix removal reagent with stirring; and washing to remove the matrix former and leave microspheres of carrier protein bound with signal precursor molecules.

Preferably, the method is carried out in aqueous solution with aqueous reagents, preferably at room temperature. The preferred method of mixing is stirring with a magnetic stirrer.

The function of the matrix former is to entrap the protein molecules in a microsphere template. The matrix former may be calcium carbonate, calcium alginate, porous silica or an oligo- or polysaccharide such as dextran. The calcium carbonate is preferably formed by adding sodium carbonate solution to a mixture of carrier protein, signal precursor molecules and calcium chloride in solution.

The size of the microspheres can be controlled by controlling the stirring speed. The density of the microspheres can be controlled by adjusting the relative proportions of carrier protein, signal precursor molecules, matrix former and reducing reagent.

As before, the microspheres may be hybrid particles in which the carrier protein and the signal precursor molecules are different. Alternatively, the carrier protein and the signal precursor may be the same. Also, the signal precursor may be direct or indirect as explained above.

Preferably, the carrier protein is selected from fibrous proteins, including but not limited to cytoskeletal proteins or extracellular matrix proteins; or globular proteins including but not limited to blood proteins, hemoproteins, cell adhesion proteins; or transport proteins, growth factors, receptor proteins, DNA-binding proteins, immune system proteins, including but not limited to mono- or polyclonal antibodies, nutrient storage/transport proteins, chaperone proteins or enzymes; or genetically modified proteins; or recombinant proteins or chemically modified protein and synthetic proteins. More preferably, the carrier protein is a protein which circulates in blood, such as bovine serum albumin.

The signal precursor molecules may be low molecular weight substances selected from the group consisting of fluorophores and their derivatives, luminophores and their derivatives, chromophores and their derivatives, prosthetic groups, or redox active substances selected from redox mediators, electrode-active substances.

Preferably, low molecular weight signal precursor molecules are fluorophores such as fluoresceins, cyanines, carbocyanines, rhodamines, xanthenes, diazo-dye based fluorescent substances, and small fluorescent aromatic and heteroaromatic molecules.

Alternatively, the low molecular weight signal precursor molecules may be chromophores such as pyrazolone, anthraquinone, carotenoid and diazo- and monoazo, oxazine, indigoid, or riboflavine based dye substances.

Most preferably, the low molecular weight signal precursor molecules are fluorescein derivatives such as fluorescein diacetate (FDA), fluorescein diacetate isothiocyanate (FDA-isothiocyanate) or fluorescein maleimide (FDA-maleimide).

High molecular weight protein signal precursor molecules include, but are not limited to, high molecular weight substances selected from the group consisting of enzymes and their precursors, bioluminogenic and fluorogenic proteins and ribozymes; peptides or proteins selected from the group consisting of antibodies including monoclonal and polyclonal antibodies, receptors, antigens, recombinant proteins, lectins, avidins, lipoproteins and glycoproteins, nucleic acids, ribozymes and aptamers.

Preferably, high molecular weight signal precursor molecules are affinity molecules such as peptides and proteins, nucleic acid strands, carbohydrates, ligands with low molecular weight and molecular imprinted polymers (MIPs) or mixtures thereof.

Alternatively, the high molecular weight signal precursor molecules may be enzymes such as peroxidase, oxidoreductase, ligase, polymerase and transferase.

Most preferably, the high molecular weight signal precursor molecules are avidin and NeutrAvidin (Trade Mark).

The method of producing the microspheres may further comprise attaching affinity molecules to the surface of the microspheres. The affinity molecules may be conjugated to the outer surface of the microspheres, e.g., by van der Waals forces, hydrogen bonds or electrostatic interactions, or they may be covalently bound to the outer surface of the microspheres, either directly or via linker molecules. If indirectly bound, the linker molecules include, but are not limited to, biomolecules, for example avidin, streptavidin, NeutrAvidin (Trade Mark), protein A, protein G, lectin or low molecular weight cross linkers. The affinity molecules may be added to the reaction mixture prior to the step of adding the matrix removal reagent.

Typical affinity molecules may be biorecognition molecules such as specific peptides and proteins, nucleic acid strands, carbohydrates, ligands with low molecular weight, receptor molecules and molecular imprinted polymers (MIPs) or mixtures thereof.

The peptides or proteins may be antibodies including monoclonal and polyclonal antibodies, receptors, antigens, lectins, avidins, oligopeptides, lipoproteins, glycoproteins, peptide hormones and allergens or parts thereof. The nucleic acids may be DNA, RNAs, oligonucleotides, ribozymes, aptamers and parts thereof. Examples of carbohydrates include mono-, oligo- and poly-saccharides, glycolipids, proteo-polysaccharides and parts thereof. The low molecular weight ligands may be biotin or biotin derivatives, steroids or hormones, cofactors or coenzymes, activators, inhibitors, pseudosubstrates or prosthetic groups of enzymes, drugs, allergens or haptens.

In a third aspect, the present invention provides a signal amplification method for detecting one or more target molecules in a sample using microspheres comprising a carrier protein bonded to signal precursor molecules, wherein said signal precursor molecules are activatable to generate a detectable signal whilst remaining bound to the carrier protein, and said microspheres having affinity molecules for specific recognition of and binding to said target molecules on the surface thereof, the method comprising:

(a) incubating the target molecules with said microspheres;

(b) separating microspheres with affinity molecule-target molecule complexes on their surface from microspheres having no affinity molecule-target molecule complexes;

(c) treating the separated microspheres with affinity molecule-target molecule complexes on their surface with a developing reagent to activate the signal precursor molecules to generate a signal, and (d) detecting or quantifying the signal.

The thus-generated signal is directly or indirectly related to the amount of the target molecules in the sample. Moreover, the signal is localised because the signal precursor molecules remain bound within the microspheres and are not released into solution. Hence, there is no dilution of the signal. On the contrary, the signal is an amplification because, for each affinity molecule-target molecule complex formed during the incubation step, there are many signal precursor molecules activated during the activation step.

Preferably, the carrier protein is selected from fibrous proteins, including but not limited to cytoskeletal proteins or extracellular matrix proteins; or globular proteins including but not limited to blood proteins, hemoproteins, cell adhesion proteins; or transport proteins, growth factors, receptor proteins, DNA-binding proteins, immune system proteins, including but not limited to mono- or polyclonal antibodies, nutrient storage/transport proteins, chaperone proteins or enzymes; or genetically modified proteins; or recombinant proteins or chemically modified protein and synthetic proteins. More preferably, the carrier protein is a protein which circulates in blood, such as bovine serum albumin.

The signal precursor molecules may be low molecular weight substances selected from the group consisting of fluorophores and their derivatives, luminophores and their derivatives, chromophores and their derivatives, prosthetic groups, or redox active substances selected from redox mediators, electrode-active substances.

Preferably, low molecular weight signal precursor molecules are fluorophores such as fluoresceins, cyanines, carbocyanines, rhodamines, xanthenes, diazo-dye based fluorescent substances, and small fluorescent aromatic and heteroaromatic molecules.

Alternatively, the low molecular weight signal precursor molecules may be chromophores such as pyrazolone, anthraquinone, carotenoid and diazo- and monoazo, oxazine, indigoid, or riboflavine based dye substances.

Most preferably, the low molecular weight signal precursor molecules are fluorescein derivatives such as fluorescein diacetate (FDA), fluorescein diacetate isothiocyanate (FDA-isothiocyanate) or fluorescein maleimide (FDA-maleimide).

High molecular weight protein signal precursor molecules include, but are not limited to, high molecular weight substances selected from the group consisting of enzymes and their precursors, bioluminogenic and fluorogenic proteins and ribozymes; peptides or proteins selected from the group consisting of antibodies including monoclonal and polyclonal antibodies, receptors, antigens, recombinant proteins, lectins, avidins, lipoproteins and glycoproteins, nucleic acids, ribozymes and aptamers.

Preferably, high molecular weight signal precursor molecules are affinity molecules such as peptides and proteins, nucleic acid strands, carbohydrates, ligands with low molecular weight and molecular imprinted polymers (MIPs) or mixtures thereof.

Alternatively, the high molecular weight signal precursor molecules may be enzymes such as peroxidase, oxidoreductase, ligase, polymerase and transferase.

Most preferably, the high molecular weight signal precursor molecules are avidin and NeutrAvidin (Trade Mark).

The affinity molecules may be biorecognition molecules such as peptides, proteins, nucleic acids, carbohydrates, ligands with low molecular weight, receptors and molecular imprinted polymers (MIPs) or mixtures thereof.

The peptides or proteins may be antibodies including monoclonal and polyclonal antibodies, receptors, antigens, lectins, avidins, oligopeptides, lipoproteins, glycoproteins, peptide hormones and allergens or parts thereof. The single stranded nucleic acids may be DNA, RNAs, oligonucleotides, ribozymes, aptamers and parts thereof. Examples of carbohydrates include mono-, oligo- and poly-saccharides, glycolipids, proteo-polysaccharides and parts thereof. The low molecular weight ligands may be biotin or biotin derivatives, steroids or hormones, cofactors or coenzymes, activators, inhibitors, pseudosubstrates or prosthetic groups of enzymes, drugs, allergens or haptens.

A particularly preferred form for the microspheres is one in which the carrier protein is bovine serum albumin (BSA) and the signal precursor molecules are selected from fluorescein diacetate (FDA), fluorescein diacetate isothiocyanate (FDA-isothiocyanate) or fluorescein diacetate maleimide (FDA-maleimide). A developing reagent is suitable for "activating" these fluorescein derivatives in the activation step, converting them to fluorescein, for example through chemical reaction, e.g. alkaline reagent, or biochemical reaction, e.g. esterase, thereby generating a detectable signal. Alternatively, the activation step may be carried out by physical means such as microwave heating, In a fourth aspect, the invention provides another signal amplification method for detecting one or more target molecules in a sample using microspheres comprising a carrier protein bound to first signal precursor molecules, wherein said first signal precursor molecules are activatable to generate a detectable signal whilst remaining bound to the carrier protein, and said microspheres having affinity molecules for specific recognition of and binding to said target molecules on the surface thereof, the method comprising:

(a) incubating the target molecules with said microspheres;

(b) separating microspheres with affinity molecule-target molecule complexes on their surface from microspheres having no affinity molecule-target molecule complexes;

(c) treating the separated microspheres with affinity molecule-target molecule complexes on their surface with a releasing reagent to disassemble the microspheres and release the first signal precursor molecules;

(d) treating the released first signal precursor molecules with a further batch of microspheres functionalised with second affinity molecules having affinity for the released first signal precursor molecules, said microspheres comprising a carrier protein bound to second signal precursor molecules, wherein said second signal precursor molecules are activatable to generate a detectable signal whilst remaining bound to the carrier protein;

(e) separating microspheres with second affinity molecule-first signal precursor molecule complexes on their surface from microspheres having no second affinity molecule-first signal precursor molecule complexes;

(f) treating the separated microspheres with second affinity molecule-first signal precursor molecule complexes on their surface with a developing reagent to activate the second signal precursor molecules to generate a signal, and (g) detecting or quantifying the signal.

The thus-generated signal is related to the amount of the target molecules in the sample. The signal is amplified many times in two different stages because, for each affinity molecule-target molecule complex formed during the incubation step (a), there are many first signal precursor molecules released in step (c) which are then incubated with a batch of different microspheres functionalised to have affinity for the first signal precursor molecules. The many first signal precursor molecules released form complexes with the different microspheres and, after removing those microspheres which have not formed complexes with the released first signal precursor molecules, an activating reagent is added to activate the many second signal precursor molecules in each of the complexed microspheres to generate a signal.

It will be appreciated that this cycle of release and re-complexing of the signal precursor molecules can be repeated many times over to achieve very significant multiples of amplification. In other words, steps (c) to (e) can be repeated from 1 to n times, where n is a positive integer, prior to carrying out steps (f) and (g), wherein at least the signal precursor molecules in the final repeat cycle are activatable to generate a detectable signal.

The target molecules represent the first analyte; the first signal precursor molecules represent the second analyte, and the second signal precursor molecules represent the tertiary analyte, and so on.

In a variant, only the signal precursor molecules in the final repeat cycle need to be activatable to generate a detectable signal. The signal precursor molecules that are released in earlier cycles need not be activatable to generate a detectable signal—they can be binding molecules such as avidin—but are regarded as signal precursor molecules because they are an important part of the cascade of reactions that ultimately lead to the signal.

High confidence and reliability can be incorporated in this amplification process by using well-understood and widely used couples such as avidin and biotin as the precursor molecule-affinity molecule pair, particularly in the later stages of the method, i.e., after the first target molecule-affinity molecule couple has been chosen to suit the particular target being detected or determined.

Note that, in the final amplification step, the signal may be localised if the ultimate signal precursor molecules remain bound within the ultimate microspheres and are not released into solution. This would minimise dilution of the signal.

On the other hand, it is not essential to detect the ultimate signal precursor molecules in their unreleased state; they can also be determined in solution, if set free, or can also provoke another amplification step. For example, if an enzyme with a high turnover rate is the ultimate signal precursor molecule, the enzyme could be allowed to work on a substrate for fluorescence or luminescence. Another example may use encapsulated FDA as the ultimate signal precursor molecule. Upon addition of a developing reagent such as aqueous sodium hydroxide, the FDA dissolves, hydrolyses and releases a large number of fluorescein molecules and thus provides an amplified fluorescence signal.

Preferably, at least for the microspheres used in incubation step (a), the carrier protein is selected from fibrous proteins, including but not limited to cytoskeletal proteins or extracellular matrix proteins; or globular proteins or blood proteins including but not limited to hemoproteins, cell adhesion proteins; or transport proteins, growth factors, receptor proteins, DNA-binding proteins, immune system proteins, including but not limited to mono- or polyclonal antibodies, nutrient storage/transport proteins, chaperone proteins or enzymes; or genetically modified proteins; or recombinant proteins and synthetic proteins. More preferably, the carrier protein is a protein which circulates in blood, such as bovine serum albumin.

Likewise, at least for the microspheres used in incubation step (a), the signal precursor molecules may be low molecular weight substances selected from the group consisting of fluorophores and their derivatives, luminophores and their derivatives, chromophores and their derivatives, prosthetic groups, or redox active substances selected from redox mediators, electrode-active substances. Preferably, low molecular weight signal precursor molecules are fluorophores such as fluoresceins, cyanines, carbocyanines, rhodamines, xanthenes, diazo-dye based fluorescent substances, and small fluorescent aromatic and heteroaromatic molecules. Alternatively, the low molecular weight signal precursor molecules may be chromophores such as pyrazolone, anthraquinone, carotenoid and diazo- and monoazo, oxazine, indigoid, or riboflavine based dye substances. Most preferably, the low molecular weight signal precursor molecules are fluorescein derivatives such as fluorescein diacetate (FDA), fluorescein diacetate isothiocyanate (FDA-isothiocyanate) or fluorescein maleimide (FDA-maleimide). High molecular weight protein signal precursor molecules include, but are not limited to, high molecular weight substances selected from the group consisting of enzymes and their precursors, bioluminogenic and fluorogenic proteins and ribozymes; peptides or proteins selected from the group consisting of antibodies including monoclonal and polyclonal antibodies, receptors, antigens, recombinant proteins, lectins, avidins, lipoproteins and glycoproteins, nucleic acids, ribozymes and aptamers. Preferably, high molecular weight signal precursor molecules are affinity molecules such as peptides and proteins, nucleic acid strands, carbohydrates, ligands with low molecular weight and molecular imprinted polymers (MIPs) or mixtures thereof. Alternatively, the high molecular weight signal precursor molecules may be enzymes such as peroxidase, oxidoreductase, ligase, polymerase and transferase. Most preferably, the high molecular weight signal precursor molecules are avidin and. NeutrAvidin (Trade Mark).

At least for the microspheres used in incubation step (a), the affinity molecules may be biorecognition molecules such as specific peptides and proteins, nucleic acid strands, carbohydrates, ligands with low molecular weight and molecular imprinted polymers (MIPs) or mixtures thereof.

The peptides or proteins may be antibodies including monoclonal and polyclonal antibodies, receptors, antigens, lectins, avidins, oligopeptides, lipoproteins, glycoproteins, peptide hormones and allergens or parts thereof. The nucleic acids may be DNA, RNAs, oligonucleotides, ribozymes, aptamers and parts thereof. Examples of carbohydrates include mono-, oligo- and poly-saccharides, glycolipids, proteo-polysaccharides and parts thereof. The low molecular weight ligands may be biotin or biotin derivatives, steroids or hormones, cofactors or coenzymes, activators, inhibitors, pseudosubstrates or prosthetic groups of enzymes, drugs, allergens or haptens.

A particularly preferred form for the ultimate microspheres is one in which the carrier protein is bovine serum albumin (BSA) and the signal precursor molecules are selected from fluorescein diacetate (FDA), fluorescein isothiocyanate (FITC) and fluorescein maleimide (FDA-maleimide). A developing reagent is suitable for "activating" these fluorescein derivatives in the activation step, converting them to fluorescein either through chemical reaction, e.g. using alkaline reagent, or through biochemical reaction, e.g. esterase, so that a detectable signal is generated.

Chemical releasing reagents used to disassemble the microspheres and release the signal precursor molecules may be small molecule reducing reagents which are effective to break the sulphur-sulphur bonds (intermolecular and intramolecular) in the microspheres. Dithiothreitol (DTT) is a particularly preferred release reagent. Disassembly of the microspheres may also be achieved through sonication, high temperature, light radiation or pH change.

Figure 1A:
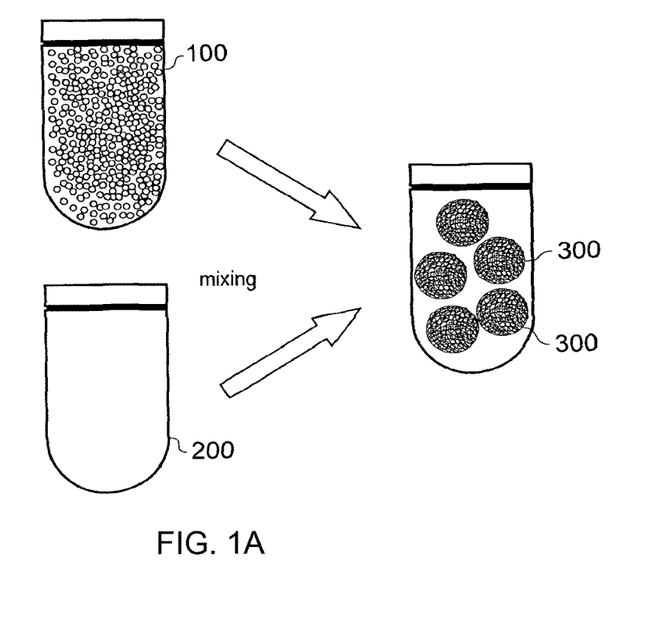
FIG. 1A is a schematic diagram illustrating a first step in the technique for fabrication of microspheres in accordance with the invention.

Referring firstly to FIG. 1, view (a) shows a first vessel 100 containing a mixed solution of calcium chloride ($CaCl_2$), carrier protein and signal precursor molecules, and a second vessel 200 containing a solution of sodium carbonate ($Na_2CO_3$). The contents of the two vessels are rapidly mixed so that the protein and signal precursor molecules, e.g. BSA-FDA, become trapped in supporting calcium carbonate ($CaCO_3$) microsphere templates 300 by co-precipitation.

Figure 1B:
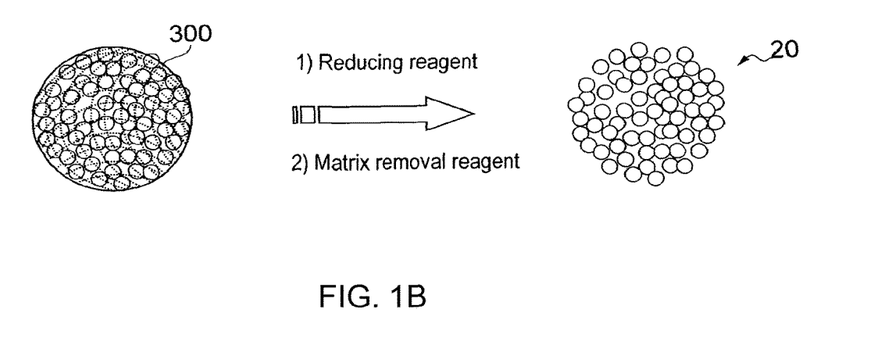
FIG. 1B illustrates the next steps in the technique for fabrication of microspheres.

View (b) illustrates what happens in the next steps. The $CaCO_3$ microsphere templates 300 with trapped protein and signal precursor molecules are treated with a reducing reagent, dithiothreitol (DTT), which causes opening of the intra-molecular disulphide bonds within the protein molecules. Then, the DTT is removed in a number of repeated washing steps. New inter-molecular and intra-molecular disulphide bonds are formed between the protein molecules. The newly-formed inter-molecular disulphide bonds contribute to the assembly of the protein molecules into microspheres 20 also containing the signal precursor molecules. The $CaCO_3$ template material is removed, leaving the protein/signal precursor molecule microspheres 20 without requiring the use of chemical crosslinkers.

Figure 2:
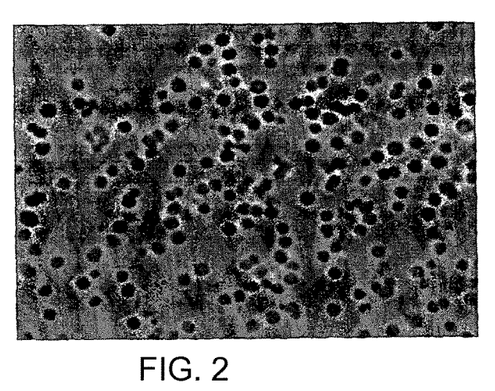
FIG. 2 is a phase contrast micrograph of protein microspheres in accordance with the first aspect of invention.

Turning now to FIG. 2, this is a phase contrast micrograph of protein microspheres produced according to the above procedure. They show good size uniformity with little deviation from an average. It is also important that the microspheres carry the same surface charge so that they do not stick together. The absence of sticking together is clearly shown in the figure. Also, a narrow size distribution is important for quantitative analysis.

Figure 3A:
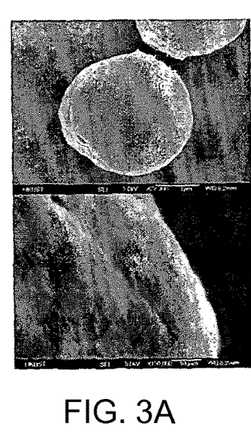
FIG. 3A shows a pair of scanning electron microscope images of protein microspheres with different porosity, including the top image shows a 22,000 magnification and the bottom image shows a 150,000 magnification.
Figure 3B:
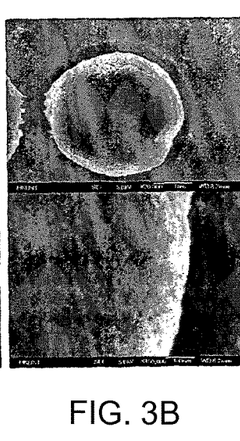
FIG. 3B shows a pair of scanning electron microscope images of protein microspheres with different porosity from those of FIG. 3A, including the top image shows a 22,000 magnification and the bottom image shows a 150,000 magnification.
Figure 3C:
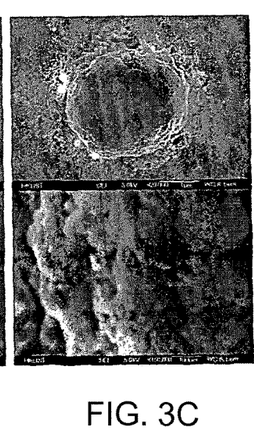
FIG. 3C shows a pair of scanning electron microscope images of protein microspheres with different porosity from those of FIGS. 3A and 3B, including the top image shows a 22,000 magnification and the bottom image shows a 150,000 magnification.

FIG. 3 shows SEM micrographs of BSA microspheres prepared using DTT concentrations ranging from 0.01 to 1 mM over a period from 15 to 60 minutes. The resulting microspheres were similar in diameter, the surface roughness and pore size of the microspheres increasing with decreasing DTT concentration.

A higher DTT concentration resulted in a higher degree of intra-molecular disulphide bond breakage within the BSA molecules, i.e., the number of free thiol groups within the protein molecules increased. After removal of DTT by washing (repeated washing steps were used), the free thiol groups within the BSA molecules self-assembled to form new inter- and intra-molecular disulphide bonds, the inter-molecular disulphide bonds contributing to the formation of protein microspheres which survived after the removal of the calcium carbonate template.

Microspheres fabricated using a low DTT concentration contained fewer inter-molecular disulphide bonds and were therefore more porous.

Figure 4A:
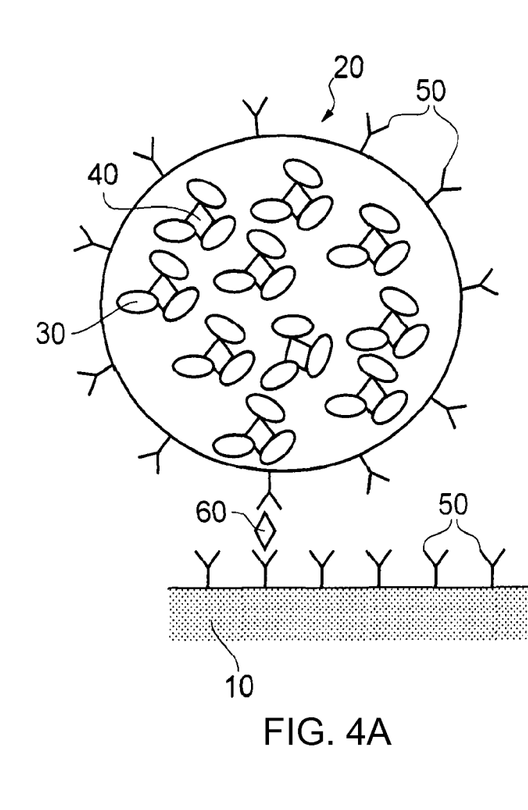
FIG. 4A is a schematic diagram showing a solid support having affinity molecules on its surface in a sandwich bioassay.
Figure 4B:
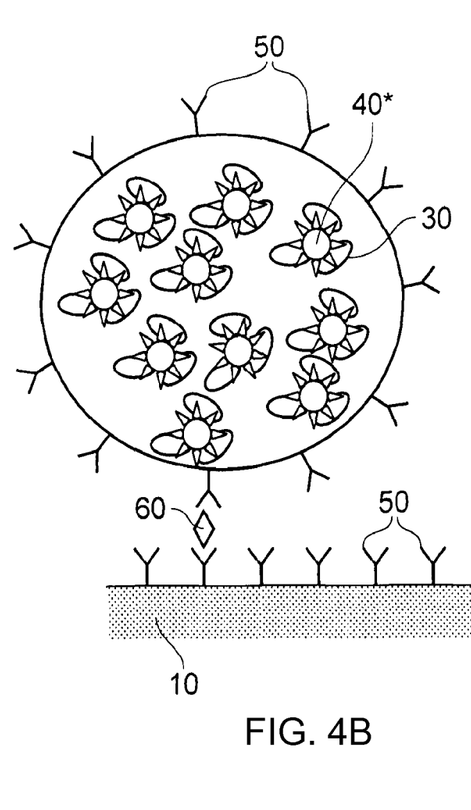
FIG. 4B is a schematic diagram showing the same microsphere, still attached to the solid support through the "sandwich" of the target molecule between two affinity molecules in a sandwich bioassay.
Figure 5A:
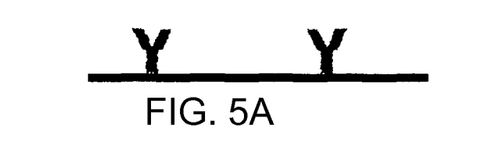
FIG. 5A is a schematic diagram of the incubation step of a solid-phase sandwich fluorescence immunoassay for BSA-FDA microspheres functionalised with goat anti-mouse IgG (Gt-α-MIgG)
Figure 5B:
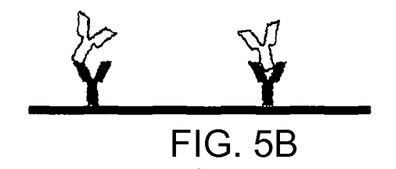
FIG. 5B is a schematic diagram of Gt-α-MIgG bound on the solid support being exposed to a solution containing the target species in a solid-phase sandwich fluorescence immunoassay for BSA-FDA microspheres functionalised with goat anti-mouse IgG (Gt-α-MIgG)
Figure 5C:
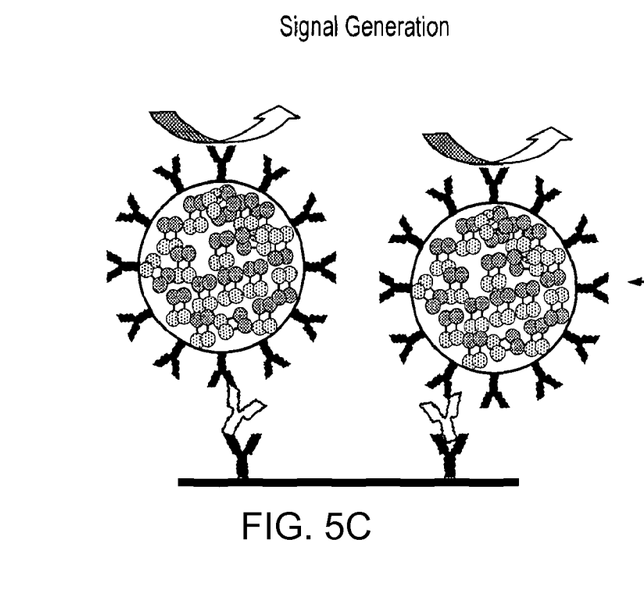
FIG. 5C is a schematic diagram of treating the captured target species with microspheres formed of BSA-FDA functionalised with Gt-α-MIgG.
Figure 5D:
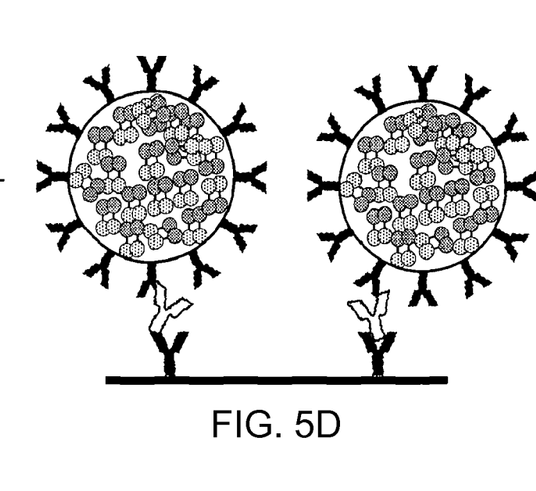
FIG. 5D is a schematic diagram of the step of adding a developing reagent so that the FDA is hydrolysed to fluoresceins to generate a localised signal which can be visualized.

Turning now to FIG. 4, this is a schematic diagram showing the working principle of the accumulation and localisation of signal in a sandwich bioassay using the microspheres of the present invention.

In view (a), a solid support 10 is shown having affinity molecules 50 on its surface. Microsphere 20 is represented here as a slightly flattened circle containing carrier proteins 30 bound to signal precursor molecules 40. Note that this is a schematic diagram and that the microsphere has been given a solid border for the purposes of illustration only. Also, the S—S binding lines between the carrier protein molecules (and the bonds between the carrier protein molecules and the signal precursor molecules) have been omitted for clarity. In reality, the microsphere is not a capsule with a solid boundary; rather, it is like a miniature sponge ball with pores extending into its interior and being formed of a uniform distribution of carrier protein molecules and signal precursor molecules bound to each other.

The microsphere 20 has affinity molecules attached 50 on its surface.

Sandwiched between one of the affinity molecules 50 on the solid support 10 and one of the affinity molecules 50 on the microsphere is a target molecule, or analyte, 60. The solid support may be a membrane, a well of a microtitre plate, a magnetic bead or, more generally, any of the solid phase platforms which are used in immunological or hybridisation assays.

In view (b), the same microsphere 20 is shown, still attached to the solid support 10 through the "sandwich" of the target molecule 60 between two affinity molecules 50. However, in this view, the microsphere 20 is shown after treatment with a developing reagent and now has signal molecules 40* represented by miniature sun symbols, where previously it had signal precursor molecules 40 represented by diamonds.

Put simply, FIG. 4(a) shows the microsphere switched off, whilst FIG. 4(b) shows the microsphere lit up.

For the purposes of illustration only, FIG. 4 shows the same type of affinity molecule 50 on the solid support 10 and on the surface of the microsphere 20. In most practical situations, however, the two affinity molecules would not be the same except when polyclonal antibodies are used or if the target analyte has repetitive epitopes.

In practice, many microsphere biolabels will become bound specifically to respective target analytes in a bioassay, depending on the size of the analyte (target) molecule and on the microsphere size. In an immunological assay, a microsphere biolabel will bind specifically to the epitope of an antigen target molecule; in a hybridisation assay, a microsphere biolabel will bind to a specific DNA-sequence target analyte.

Upon addition of a developing reagent, millions of signal generating precursor molecules within the biolabels will convert to highly fluorescent molecules and the biolabels will light up and produce a localised signal.

FIG. 5 shows schematically a solid-phase sandwich fluorescence immunoassay for BSA-FDA microspheres functionalised with goat anti-mouse IgG (Gt-α-MIgG).

In view (a), the incubation step is shown in which Gt-α-MIgG is attached to a solid support. In step (b), the Gt-α-MIgG bound on the solid support is exposed to a solution containing the target species or analyte, MIgG. The target species become captured by the bound Gt-α-MIgG. A washing step (not shown) removes target species which have not been captured. In step (c), a sandwich assay is performed by treating the captured target species with microspheres formed of BSA-FDA functionalised with Gt-α-MIgG as the affinity molecules on their surface. In another washing step (not shown), microspheres which do not become bound to captured target species are washed away. In step (d), a developing reagent is added and the FDA is hydrolysed to fluoresceins to generate a localised signal which can be visualised.

FIG. 6 schematically illustrates the principles of amplification cycling.

Figure 6A:
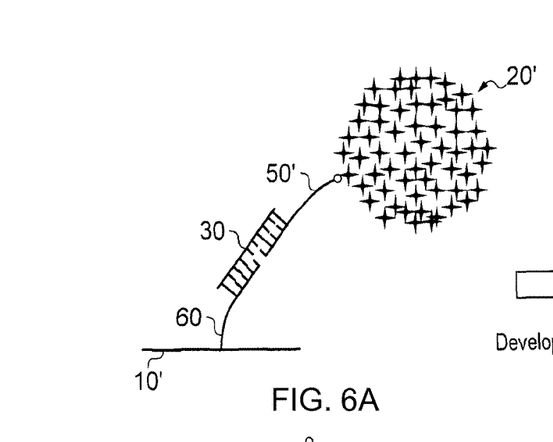
FIG. 6A is a schematic diagram illustrating a single capture molecule attached to a solid support at one of its ends and attached to a microsphere at its other end.

In view (a), a single capture molecule 60 is shown attached to a solid support 10' at one of its ends and attached to a microsphere 20' at its other end through a sandwich hybridization between a target complimentary nucleic acid 30 and the affinity molecule 50' conjugated with microsphere 20'. Schematically, the capture molecule 60 is shown as a target nucleic acid hybridised to a target complimentary nucleic acid 30 and the affinity molecule 50' conjugated with microsphere 20'.

Figure 6B:
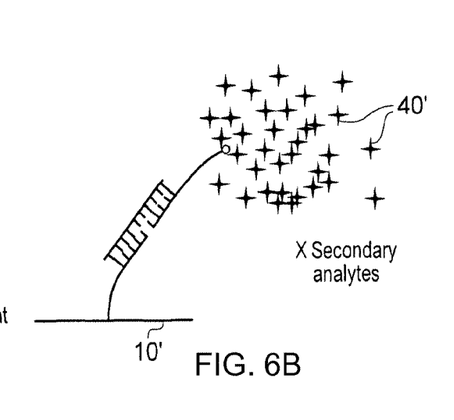
FIG. 6B is a schematic diagram illustrating the microsphere after treatment with a releasing reagent.

View (b) shows the microsphere after treatment with a releasing reagent which causes disassembly of the microsphere. In this view, the microsphere is just beginning to break up and release a multiple (X) of secondary analytes 40' into solution. The secondary analytes may be, for example, avidin.

Figure 6C:
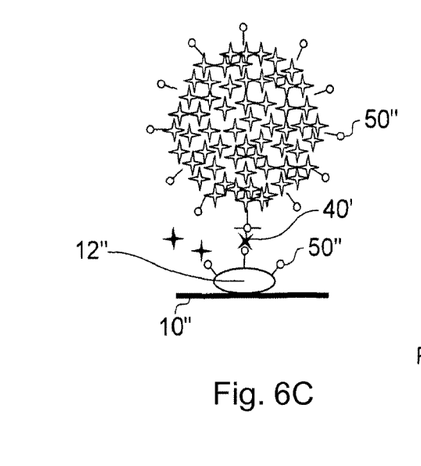
FIG. 6C is a schematic diagram illustrating a secondary analyte captured on a solid support by an affinity molecule.

In view (c), a secondary analyte 40' is shown captured on a different solid support 10" by an affinity molecule 50". In the example where the secondary analyte 40' is avidin, the affinity molecule 50" may be biotin which is bound to albumin 12". In this form, it will be attached to the solid support 10". The captured secondary analyte 40' is sandwiched between the affinity molecule 50" indirectly bound to the solid support 10" and another affinity molecule 50" bound to a different microsphere 20".

Figure 6D:
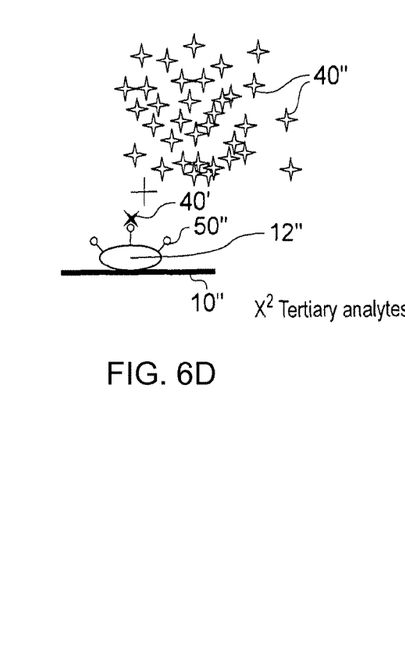
FIG. 6D is a schematic diagram illustrating the microsphere of FIG. 6C after treatment with releasing reagent which causes its disassembly.

View (d) shows the microsphere 20" after treatment with releasing reagent which causes its disassembly. In this view, the microsphere is just beginning to break up and release a multiple of secondary analytes 40". Thus, a single target molecule 60 may give rise to millions upon millions of secondary analytes after two cycles of amplification. Further cycles of amplification could be carried out, if required.

The invention will now be particularly described with reference to various examples, although it is to be understood that these are non-limiting.

Example 1

Preparation of BSA-FDA Microspheres
Step 1: Formation of a BSA Framework

A solution of BSA (10 mg/mL) in calcium chloride (0.5 mol/L) was rapidly mixed with a solution of sodium carbonate (0.5 mol/L).

Calcium carbonate was formed and, being only slightly soluble, trapped BSA in the core/interior of the calcium carbonate matrix. The calcium carbonate served as a template for entrapping BSA.

The next step was the opening of BSA intramolecular S—S bonds and the formation of new BSA intermolecular S—S bonds.

Each step comprised several washing and centrifugation cycles.

The resulting BSA-loaded calcium carbonate microspheres were incubated with dithiothreitol (DTT) solutions with concentrations ranging from 0.01 to 1 mM at pH 7.5 for 15-60 minutes at room temperature. Subsequently, the BSA-loaded calcium carbonate microspheres were washed five times with buffer (pH 7.4) by centrifugation (2000 rpm, 2 minutes) and redispersion cycles.

The addition of DTT caused reduction/breakage of intramolecular sulphur-sulphur bonds in the BSA while the removal of the DTT in these washing steps led to the formation of new intramolecular and intermolecular sulphur-sulphur bonds between BSA molecules to hold the protein together and form the microspheres.

Step 2: Binding of Signal Molecules to the BSA Framework-Matrix

To the resuspended calcium carbonate-containing microspheres was added fluorescein diacetate-5-isothiocyanate (1 mg/mL) and the reaction mixture was incubated for an hour at room temperature forming covalent bonds between BSA amino groups and the thiocyanate of fluorescein diacetate.

Step 3: Functionalisation of the BSA-FDA Microspheres

The binding of Goat-Anti-Mouse antibody to microspheres carrying the signal molecules was performed using EDC/NHS chemistry.

Step 3.1: Preparation of a Solution of the Affinity Molecules

A solution containing Goat-Anti-Mouse IgG (0.2 mg/mL) was added to 2 mM and 5 mM respectively of 1-ethyl-3(3-dimethylaminopropyl) carbodiimide (EDC) and N-hydroxy succinimide (NHS) in MES buffer at pH 7.4. The solution was allowed to react for 15 minutes at room temperature with shaking.

Step 3.2: Functionalisation of Microspheres with Antibody

After the 15 minutes of incubation, a solution of the affinity molecules activated for binding Goat-Anti-Mouse IgG was added to a pre-washed suspension of BSA-FDA microspheres and the mixture was reacted for 2 hours at room temperature with shaking. The solution of affinity molecules bound to BSA-FDA microspheres was centrifuged at 1800 rpm for 2 minutes.

The supernatant was removed and the pellet was reconstituted by 2 mL of MES buffer (pH 7.4). The BSA-FDA microspheres functionalised with affinity molecules were washed with MES buffer (pH 7.4) 3 times and re-suspended in 2 mL of MES buffer (pH 7.4).

Step 4: Removal of the Calcium Carbonate Template 10 mL of 0.2 M EDTA was then added to the BSA-FDA microsphere suspension and the whole was stirred for five minutes. EDTA treatment removed the calcium carbonate matrix from the microspheres. The reaction mixture was then subjected to centrifugation at 3000 rpm for 2 minutes at room temperature. The supernatant was removed and the antibody functionalised BSA-FDA-microspheres pellet was re-suspended into 2 mL of MES buffer (pH 7.4).

Example 2

Formation of a BSA Framework Using Calcium Alginate Matrix Former

A solution of BSA (10 mg/mL) in calcium chloride (0.5 mol/L) was rapidly mixed with a solution of sodium alginate (0.5 mol/L).

Calcium alginate was formed and, being only slightly soluble, trapped BSA in the core/interior of the calcium carbonate matrix. The calcium alginate served as a template for entrapping BSA.

The next step was the opening of BSA intramolecular S—S bonds and the formation of new BSA intermolecular S—S bonds.

Each step comprised several washing and centrifugation cycles.

The resulting BSA-loaded calcium alginate microspheres were incubated with dithiothreitol (DTT) solutions with concentrations ranging from 0.01 to 1 mM at pH 7.5 for 15-60 minutes at room temperature. Subsequently, the BSA-loaded calcium alginate microspheres were washed five times with buffer (pH 7.4) by centrifugation (2000 rpm, 2 minutes) and redispersion cycles.

The addition of DTT caused reduction/breakage of intramolecular sulphur-sulphur bonds in the BSA while the removal of the DTT in these washing steps led to the formation of new intramolecular and intermolecular sulphur-sulphur bonds between BSA molecules to hold the protein together and form the microspheres.

Example 3

Sandwich-Type Assay for the Determination of Mouse-IgG

The determination of Mouse IgG was performed in a sandwich-type assay. During the determination the Mouse IgG was specifically bound between 2 antibodies. The antibodies were the same because a polyclonal goat antibody was used. A solid phase (e.g., wells of a microtitre plate) was adsorptively coated with Goat-Anti-Mouse IgG antibodies. The second antibody was the Goat-Anti-Mouse which was bound to the BSA-FDA microspheres. This example is illustrated schematically in FIG. 5.

100 μL of Gt-α-MIgG (2 ng/μL of coating buffer) was transferred to a microtitre plate and incubated at 4° C. overnight. The microtitre plate was then washed by a washing buffer (10 mM PBS, 0.1% (w/v) BSA, 0.5% (w/v) Tween-20 (Tween is a Trade Mark)) three times. The wells were then blocked with 300 μL of post coating solution (PCS) at 37° C. for 30 minutes. 100 μL of MIgG in different concentrations (1-100 μg/L) were added to each well respectively and incubated at 37° C. for 1 hour. After washing away the unbound MIgG, a suspension of Gt-α-MIgG—{BSA-FDA Microspheres} was dispensed into the wells (100 μL/well), and the microplate was incubated again at 37° C. for 1 hour. After incubation, excess Gt-α-MIgG—{BSA-FDA Microspheres} were washed away by washing buffer. An aliquot of 100 μL of releasing solution was then added per well and the wells were measured for fluorescence intensity.

Example 4

Preparation of Avidin Microspheres

Example 4 is an example in which the carrier protein and the affinity binding molecule are one and the same molecule.
Step 1: Formation of an Avidin Framework A solution of avidin (10 mg/mL) in calcium chloride (0.5 mol/L) was rapidly mixed with a solution of sodium carbonate (0.5 mol/L).

Calcium carbonate was formed and, being only slightly soluble, precipitated and attracted/adsorbed avidin on its formed crystal surface. The calcium carbonate served as a template for the precipitation of avidin.

The next step was the crosslinking of avidin by opening its intramolecular S—S bonds and formation of avidin intermolecular S—S bonds.

Each step comprised several washing and centrifugation cycles.

The resulting avidin-loaded calcium carbonate microspheres were incubated with dithiothreitol (DTT) solutions with concentrations ranging from 0.01 to 1 mM at pH 7.5 for 15-60 minutes at room temperature. Subsequently, the avidin-loaded calcium carbonate microspheres were washed five times with buffer (pH 7.4) by centrifugation (2000 rpm, 2 minutes) and redispersion cycles.

The addition of DTT caused reduction/breakage of intramolecular sulphur-sulphur bonds in the avidin while the removal of the DTT in these washing steps led to the formation of intramolecular and intermolecular sulphur-sulphur bonds between avidin molecules to hold the protein together and form the microspheres. The reduced SH bonds in the protein undergo self-assembly formation of new intramolecular and intermolecular sulphur-sulphur bonds.
Step 2: Functionalisation of the Signal Molecules This is achieved by the binding of specific detection molecules (affinity molecules) to the avidin containing free amino groups, SH and carboxyl groups for covalent binding of the affinity molecules to the microspheres still without the affinity binding molecules.

See Example 2 above for details of the functionalisation procedure for avidin-containing microspheres.

The functionalisation procedure is much simpler with Streptavidin or a deglycosylated avidin such as NeutrAvidin (Trade Mark) because these bind directly to the target (analyte)-recognising molecule, i.e., to the affinity molecule. If Streptavidin or NeutrAvidin (Trade Mark) is used then normally biotinylated affinity molecules like e.g., biotinylated antibodies are directly bound to Streptavidin or NeutrAvidin (Trade Mark) by the strong binding power of Streptavidins to Biotin (K about $10^{16}$). Hence, chemical conjugation with e.g., EDC/NHS is not necessary.
Step 3: Dissolution of the Calcium Carbonate Out of the Microspheres This was performed by the addition of EDTA (0.2 mol/L) to a suspension of the avidin microspheres. After this procedure, the avidin signal precursor microspheres had been prepared.

Note that, as in Example 1 above, the step of removing the calcium carbonate template can be carried out before the functionalisation step.

Example 5

Solid-Phase Direct Assay (Double Amplification System, DNA Assay Model Followed by Biotin/Avidin Model)

This is an example in which the carrier protein and the affinity binding molecule are one and the same molecule and demonstrates its utility in a new signal amplification cycling technique. This example is schematically illustrated in FIG. 6.

The determination of human papilloma virus (HPV) DNA was performed in a sandwich type assay. During the determination of HPV, the DNA-strand was specifically hybridized to its complimentary nucleic acid, which was biotinylated. This hybridisation product was then reacted with microspheres made of NeutrAvidin (Trade Mark). A releasing reagent which caused the disassembly of avidin microspheres was added to release avidin into solution. The released avidin was then treated as an analyte in a subsequent solid phase direct assay.
Step 1: Solid Phase Direct Assay A (HPV DNA Model)

100 μL of HPV probes (HPV 16) were transferred to microtitre wells and incubated at 4° C. overnight. The microtitre plate was then washed with 300 μL of washing buffer five times. The wells were then blocked with 300 μL of blocking solution at 37° C. for 30 minutes. The microtitre plate was then washed with 300 μL of washing buffer five times. 30 μL of 1M NaOH and 50 μL of PCR (biotinylated HPV-virus-DNA) products in different dilutions were added to each well, respectively, and allowed to stand at room temperature for 10 minutes. 50 μL of neutralization buffer was then added and incubated at 65° C. for 30 minutes in a wet box. The microtitre plate was then washed with 300 μL of washing buffer five times. 100 μL of avidin microspheres were added into the wells respectively and incubated at 37° C. for 30 minutes. The plate was taken out after the incubation and washed five times with DNA washing buffer. 120 μL dithiothreitol (DTT) solutions with concentrations ranged from 0.01 to 1 mM at pH 7.5 were added to each well and left to stand for 15-60 minutes at room temperature. The addition of DTT caused reduction/breakage of intermolecular sulphur-sulphur bonds in the avidin, allowing the microspheres to disassemble and release avidin into solution. The released avidin molecules became the analyte ("secondary analyte") for a subsequent solid phase assay (Biotin/Avidin model).

Step 2: Solid-Phase Direct Assay B (Biotin/Avidin Model)

100 μL of BSA-Biotin (2 ng/μL of coating buffer) were directly coated on a Nunc Maxisorp 96-well microplate (Nunc is a Trade Mark of Nunc International, Rochester, N.Y.) in 0.1 mol/L carbonate buffer (pH 9.6) at 4° C. overnight. After rinsing three times with washing buffer (10 mM PBS, 0.1% (w/v) BSA, 0.5% (w/v) Tween-20 (Tween is a Trade Mark)), the wells were blocked with 300 μL of 1.0% BSA solution for half an hour at 37° C. The plate was then washed four times and corresponding solutions of "secondary analyte" (avidin) were dispensed into the wells (100 μL/well). The microplate was incubated again at 37° C. for 1 hour. After washing away the unbound secondary analyte, biotin-FDA microsphere suspension was dispensed into the wells (100 μL/well), and the microplates was incubated again at 37° C. for 1 hour. After incubation, excess biotin-FDA microspheres were washed away by washing buffer. An aliquot of 100 μL of developing reagent was then added per well for measurement of fluorescence intensity.

As will be apparent from the foregoing, the present invention is versatile and useful. The system uses simple chemistry/biochemistry and mild conditions at all times. Preparation times are not lengthy and, in the amplification scheme, many multiples of amplification can be achieved without high skills requirements, such as required for PCR.

The microsphere technology may be applied to a wide variety of detection formats, including but not limited to flow through devices, micro-fluidic devices and lateral flow devices. It may also be used with beads, both magnetic and non-magnetic, and microtitre wells.

Another application is in the fields of immunochemistry, histology and the use of the signal molecules in Western, Southern and Northern blots for the detection of cellular structures or additional bands which, up to now, could not be detected because, for example, the FITC-labelled affinity molecules worked at the limit of their analytical sensitivity.

The use of the present signal microspheres opens new possibilities in immunochemistry, histology and all the various forms of detection techniques. The classical detection principles could be improved very easily by several orders of magnitude.

Thus, the present invention may also provide various test kits for detection and/or determination of target molecules in a sample, the kit comprising microspheres comprising a carrier protein bonded to signal precursor molecules, wherein said signal precursor molecules are activatable to generate a detectable signal whilst remaining bonded to the carrier protein, said microspheres being adapted to carry on the surface affinity molecules for specific recognition of and binding to target molecules.

Another kit format may further comprise reagents for the modification of affinity molecules to make them suitable to bind to the surface of the microspheres and reagents for performing the binding reaction between the microspheres and the affinity molecules.

Another test kit format may comprise a testing device, such as a lateral flow, flow-through or dipstick device, of the type in which a fluid sample to be analysed is added to one end of an absorbent material of the testing device. The fluid is migrated to the other end by capillary forces, optionally enhanced by a sucking pad positioned at said other end. Detector antibodies labelled with microspheres (containing the signal generating substance) are loosely bound in excess at the starting point of the testing device.

The signal-generating substance can be a fluorescent dye, a visible dye, a bioluminescent or chemiluminescent material, a magnetic material, or an enzyme.

The antigen from the sample is interacted with the detector antibodies and migrates to the other end of the device carrying along the microspheres. A sandwich is formed with catcher antibodies in the indicator region (dot or stripe) near the sucking pad. Here, catcher antibodies are more tightly bound to the absorbent material and therefore cannot migrate.

The more analyte is present in the sample, the more sandwich structures are formed and the more microspheres are bound in the indicator region. The signal generating substance can be activated by various procedures, depending on the structure of the signal precursor molecules. For example, for FDA used as the signal precursor, it would be possible to dip the whole device into an alkaline activating solution or to drop an alkaline activator onto the indicator region.

A portion of the detector antibodies (labelled with microspheres) is not bound to the indicator region and proceeds with migration. A control region placed behind the indicator region shows whether the solid phase reaction is working properly.

The sandwich-like solid phase/membrane based technology can be modified for low-molecular weight substances using competitive assay principles.

Various modifications may be made to the invention without departing from the scope of the claims which follow.

What is claimed:

1. A method for detecting one or more target molecules in a sample using microspheres formed of a uniform distribution of carrier protein molecules and signal precursor molecules bound to each other, wherein said carrier protein molecules are linked covalently by intermolecular disulfide bonds to form a porous matrix, said signal precursor molecules are activatable to generate a detectable signal whilst remaining bonded to the carrier protein, and said microspheres have affinity molecules for specific recognition of and binding to said target molecules on the surface thereof, the method comprising:
   (a) incubating the target molecules with said microspheres;
   (b) separating microspheres having affinity molecule-target molecule complexes on their surface from microspheres having no affinity molecule-target molecule complexes;
   (c) treating the separated microspheres with affinity molecule-target molecule complexes on their surface with a developing reagent to activate the signal precursor molecules to generate a signal, and
   (d) detecting or quantifying the signal.

2. The method of claim 1, wherein the carrier protein is bovine serum albumin (BSA) and the signal precursor molecules are fluorescein diacetate (FDA).

3. The method of claim 2, wherein the developing reagent is a base or esterase.

\* \* \* \* \*